(12) United States Patent
Terashima

(10) Patent No.: US 10,589,364 B2
(45) Date of Patent: Mar. 17, 2020

(54) DRILL

(71) Applicant: TOKO CO., LTD., Bunkyo-Ku, Tokyo (JP)

(72) Inventor: Makoto Terashima, Tokyo (JP)

(73) Assignee: Toko Co., Ltd., Tokyo (JP)

( * ) Notice: Subject to any disclaimer, the term of this patent is extended or adjusted under 35 U.S.C. 154(b) by 0 days.

(21) Appl. No.: 16/301,566

(22) PCT Filed: Jun. 22, 2017

(86) PCT No.: PCT/JP2017/023021
§ 371 (c)(1),
(2) Date: Nov. 14, 2018

(87) PCT Pub. No.: WO2017/222011
PCT Pub. Date: Dec. 28, 2017

(65) Prior Publication Data
US 2019/0299302 A1    Oct. 3, 2019

(30) Foreign Application Priority Data

Jun. 22, 2016   (JP) .................................. 2016-123701

(51) Int. Cl.
*B23B 51/02* (2006.01)
*A61B 17/16* (2006.01)

(52) U.S. Cl.
CPC .............. *B23B 51/02* (2013.01); *A61B 17/16* (2013.01); *B23B 2251/04* (2013.01); *B23B 2251/18* (2013.01); *Y10T 408/9097* (2015.01)

(58) Field of Classification Search
CPC .. B23B 51/02; B23B 2251/04; B23B 2251/18
See application file for complete search history.

(56) References Cited

U.S. PATENT DOCUMENTS

| | | | | |
|---|---|---|---|---|
| 2,600,286 A | * | 6/1952 | Weiland | B27G 15/00 408/211 |
| 3,443,459 A | * | 5/1969 | Mackey, Jr. | B23B 51/02 408/230 |
| 3,779,664 A | * | 12/1973 | Caley | B23B 51/02 408/225 |
| 5,217,332 A | * | 6/1993 | Takasaki | B23B 51/00 408/144 |
| 7,988,389 B2 | * | 8/2011 | Miebach | B23B 51/02 408/211 |
| 2010/0166517 A1 | | 7/2010 | Saito et al. | |

(Continued)

FOREIGN PATENT DOCUMENTS

| | | | | |
|---|---|---|---|---|
| DE | 102008029404 A1 | * | 12/2009 | ............. B23B 51/02 |
| EP | 1958719 A1 | * | 8/2008 | ............. B23B 37/00 |

(Continued)

*Primary Examiner* — Eric A. Gates
(74) *Attorney, Agent, or Firm* — Carrier Blackman & Associates, P.C.; William D. Blackman; Joseph P. Carrier

(57) ABSTRACT

A drill includes a tip cutting edge provided at a tip end thereof and a main cutting edge continuous to a rearward of the tip cutting edge. A point angle of the tip cutting edge is a predetermined acute angle. A point angle of the main cutting edge decreases from a front end toward a rear end of the main cutting edge. A point angle at the front end of the main cutting edge is an acute angle greater than the point angle of the tip cutting edge.

4 Claims, 3 Drawing Sheets

(56) References Cited

U.S. PATENT DOCUMENTS

| | | |
|---|---|---|
| 2010/0241129 A1 | 9/2010 | Markey et al. |
| 2012/0093600 A1 | 4/2012 | Sampath et al. |
| 2012/0263548 A1 | 10/2012 | Harris |
| 2014/0364855 A1 | 12/2014 | Stoll et al. |

FOREIGN PATENT DOCUMENTS

| | | | | |
|---|---|---|---|---|
| EP | 2390028 A1 | * | 11/2011 | ............. B23B 51/02 |
| JP | S64-50911 U | | 3/1989 | |
| JP | 05069214 A | * | 3/1993 | |
| JP | 06179109 A | * | 6/1994 | |
| JP | 2002200510 A | * | 7/2002 | |
| JP | 2003191211 A | * | 7/2003 | |
| JP | 3940002 B2 | | 7/2007 | |
| JP | 2012-135873 A | | 7/2012 | |
| JP | 5341502 B2 | | 11/2013 | |
| JP | 2016179543 A | * | 10/2016 | |
| SU | 1156865 A | * | 5/1985 | |
| WO | 2015/182618 A1 | | 12/2015 | |

\* cited by examiner

DRILL

TECHNICAL FIELD

The present invention relates to a drill including a tip cutting edge provided at a tip end thereof and a main cutting edge continuous to a rearward of the tip cutting edge.

BACKGROUND ART

Conventionally, there is known a drill in which a point angle of a cutting edge decreases from a tip end toward a rear end of the cutting edge (e.g., refer to Patent Literature 1 and 2). In the drill in Patent Literature 1, the point angle of the cutting edge is an acute angle and decreases in two steps. The point angle on the tip end side is approximately 70° while the point angle on the rear end side is approximately 20°.

According to Patent Literature 1, when a drilled hole penetrating a wall material is to be provided, a large part of the drilled hole is efficiently drilled by the tip end side of the cutting edge having the larger point angle, and at the last step, the hole is cut and broadened by the rear end side of the cutting edge having the smaller point angle without causing breakage, enabling to provide an accurate through hole.

Also, in the drill in Patent Literature 2, the point angle of the cutting edge continuously (smoothly) decreases from the tip end (center position) toward the rear end (maximum diameter position) of the cutting edge, and a clearance angle of the cutting edge continuously decreases from the center position toward the maximum diameter position. According to Patent Literature 2, while abrasion resistance of the cutting edge is improved, the part at the maximum diameter position forms a cutting edge portion for reaming, which enables to conduct reaming by means of the cutting edge.

CITATION LIST

Patent Literature

Patent Literature 1: JP S64-50911 Y
Patent Literature 2: JP 2012-135873 A

SUMMARY OF INVENTION

Technical Problem

However, the aforementioned drills in Patent Literatures 1 and 2 may be inappropriate in a case in which a drilled hole is provided in a bone or the like in medical practice.

That is, in a case of drilling a hole in a femur, there is a case in which the hole must be drilled in the femur at a low angle at which the drill axis is angled at about 30° with respect to the femur axis. In such a case, according to each of the aforementioned drills in Patent Literature 1 and 2, when the drill is attached to a hand drill and is rotated to start drilling the hole, the surface of the bone is kicked by the cutting edge of the drill. Accordingly, it is difficult to position the drill at a correct drilling position and start the drilling.

In consideration of the above conventional problems, an object of the present invention is to provide a drill which can be positioned at a drilling position and can start drilling with no difficulty even in a case in which drilling is conducted at a low angle.

Solution to Problem

A drill as a first invention includes a tip cutting edge provided at a tip end and a main cutting edge connected to a rearward of the tip cutting edge, in which a point angle of the tip cutting edge is a predetermined acute angle, a point angle of the main cutting edge decreases from a front end toward a rear end of the main cutting edge, a point angle at the front end of the main cutting edge is an acute angle greater than the point angle of the tip cutting edge, and a part at which the tip cutting edge is connected to the main cutting edge is bent in a direction of being away from a center axis of the drill from the tip cutting edge toward the main cutting edge.

According to the first aspect of the invention, the drill includes at the tip end the tip cutting edge having a smaller point angle than the point angle at the front end of the main cutting edge, which is an acute angle. Accordingly, in a case in which an approach angle (an angle between a surface of a drilled target and a drill axis) of the drill does not cause the main cutting edge to contact the drilled target when the tip end of the drill is positioned to a drilling start position of the drilled target, the tip end can reliably be positioned to the drilling start position to start drilling.

Also, since the point angle of the main cutting edge decreases from the front end toward the rear end and is smaller than the aforementioned acute angle, the drill can be configured easily so that the aforementioned approach angle of the drill that does not cause contact may be a desired small angle such as 30° or less.

Consequently, by appropriately selecting the point angles and the dimensions of the tip cutting edge and the main cutting edge within a range according to the configuration of the present invention, it is possible to easily provide a drill which can be positioned and can start drilling with no difficulty even in a case in which drilling is conducted at a low angle.

Further, with the drill, at the time of start of drilling, the position of the tip end of the drill with respect to the drilling position is reliably secured by drilling by the tip cutting edge, and subsequent drilling can be followed by drilling by the main cutting edge. In the drilling by the main cutting edge, the front end of the main cutting edge having a larger point angle can advance drilling in a favorable manner, and the rear end part of the main cutting edge having a smaller point angle can finish the drilled hole with high accuracy.

In the drill as a second aspect of the invention according to the first aspect of the invention, the main cutting edge includes a first part, a second part, and a third part in this order from a tip end side, the first part has a constant first point angle, the second part has a constant second point angle smaller than the first part, and the third part has a third point angle continuously decreasing from an angle equal to or smaller than the second point angle toward the rear end.

According to the second aspect of the invention, since the first part and the second part of the main cutting edge respectively have the constant point angles, the main cutting edge can be processed and formed easily. Also, since the third point angle of the third part of the main cutting edge continuously decreases, the drilled hole can be finished by the third part with high accuracy.

In the drill as a third aspect of the invention according to the first aspect of the invention, the point angle of the main cutting edge continuously decreases from the tip end toward the rear end of the main cutting edge.

According to the third aspect of the invention, drilling of the drilled hole can efficiently advance on the tip end side of the main cutting edge having a large point angle, and the drilled hole can be finished accurately on the rear end side of the main cutting edge having a small point angle. Also, since the main cutting edge has no corner portion that easily causes a loss and abrasion, durability of the main cutting edge can be improved.

In the drill as a fourth aspect of the invention according to any one of the first to third aspects of the invention, the point angle of the tip cutting edge is 30° to 50°, and the point angle at the front end of the main cutting edge is 60° to 90°.

According to the fourth aspect of the invention, it is possible to more easily provide a drill the tip end of which can reliably be positioned at the drilling position and which can start drilling without causing the main cutting edge to contact the drilled target even in a case in which the approach angle of the drill is small to some extent.

DESCRIPTION OF EMBODIMENTS

Figure 1:
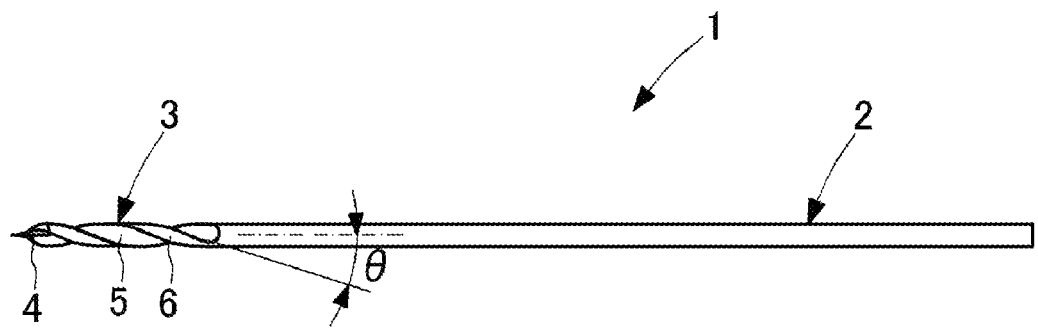
FIG. 1 is a front view of a drill according to an embodiment of the present invention.

Hereinbelow, an embodiment of the present invention will be described with reference to the drawings. A drill 1 according to an embodiment of the present invention includes a shank 2 adapted to attach the drill 1 to a drill chuck and a body 3 located further on a tip end side than the shank 2, as illustrated in FIG. 1. The shape of the shank 2 is defined to fit with the shape of the drill chuck. The body 3 is provided with a tip end portion 4 including two cutting edges, and a flute 5 and a land 6 continuing into a rearward of the tip end portion 4 and adapted to evacuate drilling chips.

Figure 2:
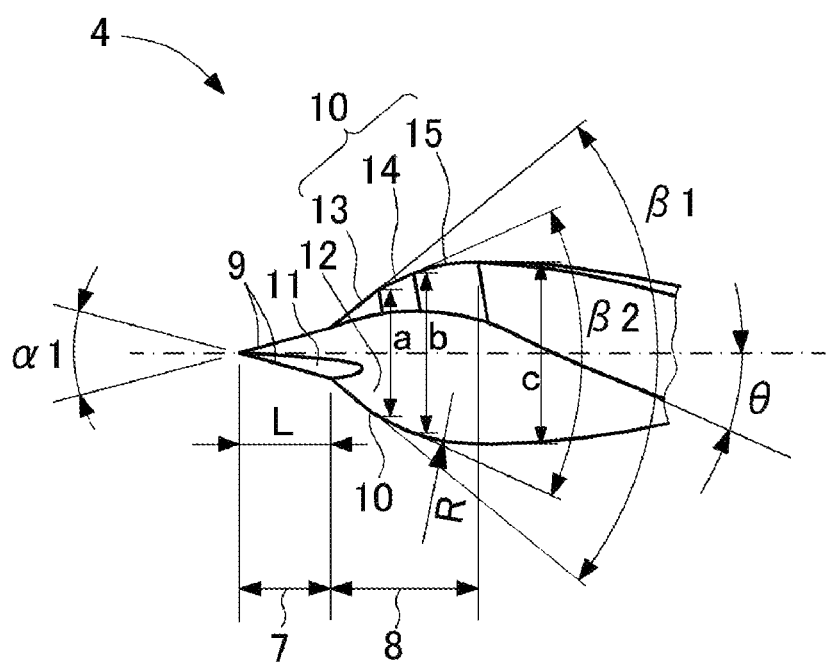
FIG. 2 is a front view of a tip end portion of the drill in FIG. 1.

As illustrated in FIG. 2, the tip end portion 4 includes a tip positioning portion 7 provided furthest on the tip end side and mainly contributing to reliable positioning to a drilled target and a main drilling portion 8 continuing to a rearward of the tip positioning portion 7 and adapted to conduct main drilling to provide a drilled hole.

The tip positioning portion 7 includes a tip cutting edge 9 for drilling adapted to insert the tip positioning portion 7 positioned at a drilling position of the drilled target into the drilled target to secure the drilling position. The main drilling portion 8 includes a main cutting edge 10 continuing to a rearward of the tip cutting edge 9. That is, each of the two cutting edges of the tip end portion 4 are constituted by the tip cutting edge 9 located furthest on the tip end side and the main cutting edge 10 located on the rear side of the tip cutting edge 9.

Figure 3:
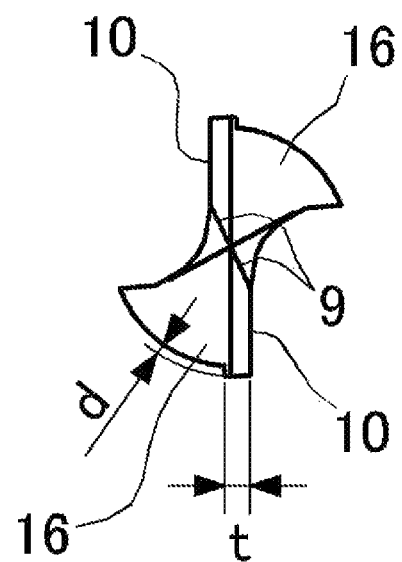
FIG. 3 is a side view of the tip end portion of the drill in FIG. 1.

As illustrated in FIG. 3, when the tip end portion 4 of the drill 1 is seen along an axial direction of the drill 1 (hereinbelow referred to simply as "an axial direction"), the tip cutting edge 9 is inclined to the main cutting edge 10. In FIG. 2, an angle $\alpha 1$ made by the tip cutting edge 9 represents a point angle of the tip cutting edge 9.

Figure 4:
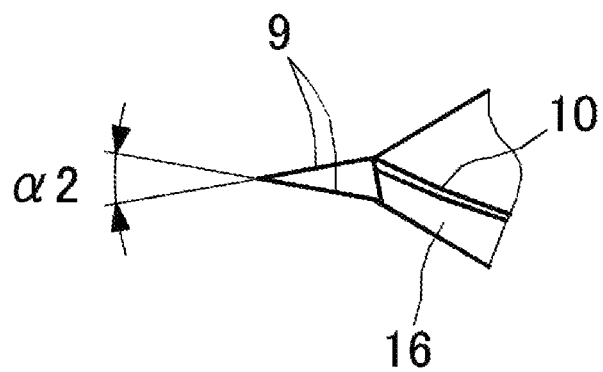
FIG. 4 is a plan view of the tip end portion of the drill in FIG. 1.
Figure 5:
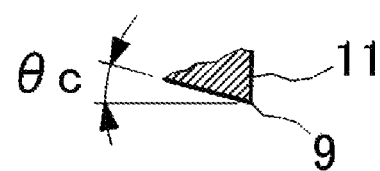
FIG. 5 is a cross-sectional view illustrating a clearance angle of a tip cutting edge of the drill in FIG. 1.

Typically, in the front view in FIG. 2, the angle $\alpha 1$ made by the tip cutting edge 9 (point angle) is approximately 40°. In the plan view in FIG. 4, an angle $\alpha 2$ made by the tip cutting edge 9 (point angle) is approximately 26°. Also, as in FIG. 5, a clearance angle $\theta c$ of the tip cutting edge 9 is approximately 20°. A rake angle of the tip cutting edge 9 is approximately 0°. A rake surface 11 of the tip cutting edge 9 is connected to a rake surface 12 of the main cutting edge 10 as in FIG. 2.

A point angle of the main cutting edge 10 decreases from a front end toward a rear end of the main cutting edge 10, and at the front end, the point angle of the main cutting edge 10 is an acute angle $\beta 1$ greater than the point angle $\alpha 1$ of the tip cutting edge 9. The main cutting edge 10 includes a first part 13, a second part 14, and a third part 15 in this order from the tip end side.

That is, the first part 13 has a constant first point angle $\beta 1$, the second part 14 has a constant second point angle $\beta 2$ smaller than the first point angle $\beta 1$, and the third part 15 has a third point angle continuously changing from an angle equal to or smaller than the second point angle $\beta 2$ to 0°. The dimensions of the tip positioning portion 7 and the first part 13, the second part 14, and the third part 15 of the main cutting edge 10, and the values of the first point angle $\beta 1$ and the second point angle $\beta 2$, are selected in consideration of the following points.

That is, these are selected so that, in a case in which drilling is conducted in a femur at a low angle at which an approach angle (an angle between the drill axis and the femur axis or surface) is approximately 30°, the main cutting edge 10 may not contact the femur when the drill 1 is positioned to the drilling position of the femur by means of the tip positioning portion 7 including the tip cutting edge 9. Also, these are selected so that the low-angle drilling may be conducted efficiently and accurately.

Typically, for example, as seen in FIG. 2, the angle $\alpha 1$ of the tip cutting edge 9 is 40°, and a length L of the tip positioning portion 7 in the axial direction is 2.3 mm. A maximum diameter a of the first part 13 of the main cutting edge 10 is 3.2 mm, the first point angle $\beta 1$ is 77°, a maximum diameter b of the second part 14 is 4.0 mm, and the second point angle $\beta 2$ is 48°. The third part 15 is formed in a spherical strip-like shape having a radius R of 5.0 mm, and a maximum diameter c of the third part 15 is 4.5 mm.

The dimensions and angles of the respective parts are not limited to those described above and can be preferred values in accordance with the drilled target and the usage on condition that these values conform to the present invention. That is, the point angle $\alpha 1$ of the tip cutting edge 9 corresponds to a value within a range of approximately 20° to 50°. In a case in which the drill 1 is used for medical purposes, the drill 1 is made of stainless steel, for example. Thus, in a case in which the point angle $\alpha 1$ is 20° or greater, the tip cutting edge 9 will not be broken.

In a case in which the approach angle of the drill 1 does not need to be too small, or in which the tip end of the drill 1 does not need to be too sharp, a preferred range of the point angle $\alpha 1$ is 30° to 50°. The reason for this is that the greater point angle $\alpha 1$ can prevent the edge tip from crushing. In a case in which the prevention of crushing of the edge tip is considered at the same time as a certain degree of sharpness of the tip end of the drill 1 is secured, a more preferred range of the point angle $\alpha 1$ is 35° to 45°, and a further preferred range is 38° to 42°.

Also, a preferred range of the first point angle β1 is 60° to 90°, a more preferred range is 72° to 82°, and a further preferred range is 75° to 79°. A preferred range of the second point angle β2 is 43° to 53°, and a more preferred range is 46° to 50°.

Also, for a flank 16 of the main cutting edge 10, a second clearance angle in the radial direction is 20°, a third clearance angle in the radial direction is 40°, a second clearance angle in the axial direction is 10°, and a third clearance angle in the axial direction is 15°. As a rake angle of the main cutting edge 10, an angle such as around 0° is selected. However, the clearance angles and the rake angle are not limited to these values and are arbitrarily determined in consideration of the drilling efficiency, the operability, the drilling accuracy, and the like.

As for typical values for the dimensions of other parts, a helix angle θ is 20°, a web thickness is 0.9 mm, a web taper is 1/100, and a flute/land ratio is 1:1.2. Also, as in FIG. 3, a margin width t is 0.4 mm, and a depth of body clearance d is 0.1 mm. The drill 1 is typically in a right-hand cut and right-hand helix type and has no back taper.

In this configuration, in a case in which a drilled hole is provided in a femur serving as a drilled target with use of a hand drill to which the drill 1 is attached, the tip positioning portion 7 of the drill 1 is placed at a drilling position of the drilled target for positioning. At this time, even in a case in which drilling is conducted at a low angle, the main cutting edge 10 does not contact the femur, and the point angle α1 of the tip cutting edge 9 of the tip positioning portion 7 is approximately 40°. Accordingly, positioning can be performed easily.

Thereafter, when the drill 1 is rotated, the tip cutting edge 9 of the tip positioning portion 7 starts drilling a hole. At this time, the main cutting edge 10 has not contacted the drilled target, and the drilled target is not kicked by the main cutting edge 10. Hence, the tip positioning portion 7 cuts into the drilled target without departing from the drilling position and secures the drilling position.

When drilling by means of the tip cutting edge 9 advances to some extent, the main cutting edge 10 contacts the femur and starts contributing to drilling. At this time, since the tip positioning portion 7 enters the femur and secures the position of the drill 1, the drill 1 will not depart from the drilling position even when the main cutting edge 10 contacts the drilled target.

Since the front end of the main cutting edge 10 has a relatively large but acute point angle as described above, drilling thereafter advances while the diameter is efficiently expanded by the part of the main cutting edge 10 on the front end side with relatively low drilling resistance.

As the drilling advances, the third part 15 of the main cutting edge 10 starts contributing to drilling, and highly accurate drilling is sequentially conducted by the small point angle of the third part 15. Consequently, when the drilling is completed, a highly accurate drilled hole is made.

As described above, according to the present embodiment, the tip positioning portion 7 including the tip cutting edge 9 having a point angle of approximately 40° can reliably position the drill 1 at the drilling position and secure the drilling position.

At this time, since the point angle of the main cutting edge 10 decreases as described above, it is possible, in a case in which the drilled target is drilled at a low angle, to prevent positioning of the drill 1 from being interrupted due to contact of the main cutting edge 10 with the drilled target and to prevent the drill 1 from departing from the drilling position.

Accordingly, even in a case in which drilling is conducted to a femur or the like at a low angle, drilling can be started with no difficulty. Once drilling is started in a state in which the drill 1 is positioned, the part of the main cutting edge 10 on the front end side having a relatively large point angle can effectively advance drilling, and the part of the main cutting edge 10 on the rear end side having a small point angle can make a drilled hole with high accuracy.

Also, since the main cutting edge 10 is configured to include the first part 13 and the second part 14 having constant point angles, the main cutting edge 10 can be processed and formed easily.

Also, since the third part of the main cutting edge 10 is configured so that the point angle may continuously change from an angle equal to or smaller than the point angle of the second part 14 to 0°, a drilled hole can be finished with high accuracy.

Although the embodiment of the present invention has been described above, the present invention is not limited to this. For example, the point angle of the main cutting edge 10 may continuously (generally smoothly) decrease from the tip end portion toward the rear end of the main cutting edge 10.

According to this example, drilling can effectively advance on the tip end side of the main cutting edge 10, and a drilled hole can be finished accurately on the rear end side of the main cutting edge 10. Also, since the main cutting edge 10 has no corner portion that easily causes a loss and abrasion, durability of the main cutting edge 10 can be improved.

Also, the drill 1 can favorably be used not only for medical purposes such as for drilling of a femur but also for drilling of resin, metal, and the like. Also, even in a case in which the drill 1 is used for medical purposes, the drill 1 can favorably be used for drilling of a skull, a facial bone, a bone of a finger, and the like instead of the femur.

Also, the dimensions and angles of the respective parts of the drill 1 are not limited to those described in the above embodiment and can be various values in accordance with the diameter of the drill 1, the usage, the material of the processed object, and the like.

REFERENCE SIGNS LIST

1 drill
2 shank
3 body
4 tip end portion
5 flute
6 land
7 tip positioning portion
8 main drilling portion
9 tip cutting edge
10 main cutting edge
11, 12 rake surface
13 first part
14 second part
15 third part
16 flank

The invention claimed is:

1. A drill comprising:
   a tip cutting edge provided at a tip end; and
   a main cutting edge connected to a rearward end portion of the tip cutting edge,
   wherein:
   a point angle of the tip cutting edge is a predetermined acute angle, a point angle of the main cutting edge decreases from a front end toward a rear end of the main cutting edge, a point angle at the front end of the main cutting edge is an acute angle greater than the point angle of the tip cutting edge, the main cutting edge includes a first part, a second part, and a third part in this order from a tip end side, the first part has a constant first point angle, the second part has a constant second point angle smaller than the first part, and the third part has a third point angle, decreasing continuously toward the rear end thereof, from an angle equal to or smaller than the second point angle.

2. The drill according to claim 1, wherein the point angle of the tip cutting edge is in a range of 30° to 50°, and the point angle at the front end of the main cutting edge is in a range of 60° to 90°.

3. A drill comprising:
a tip cutting edge provided at a tip end; and
a main cutting edge connected to a rearward end portion of the tip cutting edge,
wherein:
a point angle of the tip cutting edge is a predetermined acute angle in a range of 30° to 50°,
a point angle of the main cutting edge, in relation to the center axis of the drill, decreases from a front end toward a rear end of the main cutting edge, and
a point angle at the front end of the main cutting edge is an acute angle greater than the point angle of the tip cutting edge and is in a range of 60° to 90°.

4. The drill according to claim 3, wherein the point angle of the main cutting edge decreases continuously from the tip end toward the rear end of the main cutting edge.

\* \* \* \* \*